(12) United States Patent
Chu

(10) Patent No.: US 11,602,262 B2
(45) Date of Patent: Mar. 14, 2023

(54) MEDICAL SYSTEMS, DEVICES, AND RELATED METHODS

(71) Applicant: Boston Scientific Scimed, Inc., Maple Grove, MN (US)

(72) Inventor: Michael S. H. Chu, Brookline, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 998 days.

(21) Appl. No.: 15/870,245

(22) Filed: Jan. 12, 2018

(65) Prior Publication Data

US 2018/0199799 A1    Jul. 19, 2018

Related U.S. Application Data

(60) Provisional application No. 62/447,549, filed on Jan. 18, 2017.

(51) Int. Cl.
*A61B 1/00*        (2006.01)
*A61B 1/012*       (2006.01)
(Continued)

(52) U.S. Cl.
CPC ........ *A61B 1/00147* (2013.01); *A61B 1/0052* (2013.01); *A61B 1/00066* (2013.01);
(Continued)

(58) Field of Classification Search
CPC ........ A61B 2090/064; A61B 2090/065; A61B 2090/066; A61B 2090/068; A61M 2205/332
See application file for complete search history.

(56) References Cited

U.S. PATENT DOCUMENTS 5,713,897 A * 2/1998 Goble ................... A61F 2/0805
                                                    606/1
6,171,310 B1 * 1/2001 Giordano .............. A61F 2/0811
                                                    606/53
(Continued)

FOREIGN PATENT DOCUMENTS

CN      104619270 A    5/2015
CN      105208949 A    12/2015
EP       1704822 A1    9/2006

OTHER PUBLICATIONS

Official Action dated Jun. 11, 2021 in corresponding Chinese Application No. 201880006155.2 with English Translation (16 pages).

*Primary Examiner* — Rex R Holmes
*Assistant Examiner* — Sana Sahand
(74) *Attorney, Agent, or Firm* — Bookoff McAndrews, PLLC

(57) ABSTRACT

A device may include a first portion coupled to a shaft of an insertable medical device. The first portion may extend along a first portion longitudinal axis between a proximal end and a distal end. The first portion may include a protrusion extending radially outwardly of the first portion longitudinal axis. At least a portion of the first portion may be received within a lumen of a second portion. The second portion may be axially moveable along the first portion longitudinal axis relative to the first portion. The second portion may include a longitudinally extending channel. A spring may be located radially between the first portion and the second portion.

5 Claims, 5 Drawing Sheets

(51) Int. Cl.
  *A61B 5/00*     (2006.01)
  *A61B 1/005*    (2006.01)
  A61B 34/30      (2016.01)
  A61B 90/00      (2016.01)

(52) U.S. Cl.
  CPC .......... *A61B 1/00135* (2013.01); *A61B 1/012* (2013.01); *A61B 5/6847* (2013.01); *A61B 5/6874* (2013.01); *A61B 5/6885* (2013.01); A61B 1/00071 (2013.01); A61B 5/6852 (2013.01); A61B 2034/301 (2016.02); A61B 2090/064 (2016.02); A61M 2205/332 (2013.01)

(56) References Cited

U.S. PATENT DOCUMENTS

| | | | |
|---|---|---|---|
| 6,981,945 | B1 | 1/2006 | Sarvazyan et al. |
| 2009/0306472 | A1* | 12/2009 | Filipi .................... A61M 29/00 600/104 |
| 2011/0065991 | A1 | 3/2011 | Sarvazyan et al. |
| 2012/0184955 | A1 | 7/2012 | Pivotto et al. |
| 2012/0203168 | A1 | 8/2012 | Fujimoto et al. |
| 2012/0259203 | A1* | 10/2012 | Devereux ......... A61M 25/0631 600/106 |
| 2013/0096566 | A1* | 4/2013 | Bowen ................ A61B 5/4504 606/102 |
| 2015/0208974 | A1 | 7/2015 | Teoh |
| 2015/0297864 | A1 | 10/2015 | Kokish et al. |
| 2015/0327878 | A1* | 11/2015 | Chu ....................... A61B 90/03 606/127 |

* cited by examiner

MEDICAL SYSTEMS, DEVICES, AND RELATED METHODS

CROSS-REFERENCE TO RELATED APPLICATIONS

This patent application claims the benefit of priority under 35 U.S.C. § 119 to U.S. Provisional Patent Application No. 62/447,549, filed Jan. 18, 2017, which is herein incorporated by reference in its entirety.

TECHNICAL FIELD

Various aspects of the present disclosure relate generally to medical systems, devices, and related methods. More specifically, the present disclosure relates to medical systems and/or devices for measuring applied force via a shaft or elongate member of a device during insertion and/or withdrawal of the shaft or elongate member.

BACKGROUND

The field of endoscopy covers systems and methods a user may employ to examine and/or treat a patient with, e.g., the assistance of an endoscope or other suitable introduction sheaths or devices. An endoscope (or other suitable introduction device) may provide for viewing of, for example, the interior of a hollow organ or cavity in the patient's body. Ureteroscopy, for example, may be performed to diagnose and treat urinary tract diseases and ureteral strictures. A ureteroscope may be inserted retrograde through the urinary tract such that diagnosis and treatment of urinary tract abnormalities may be performed. Insertion and withdrawal of a shaft of a ureteroscope or other such endoscope or medical device must be done carefully to avoid excessive application of force or insufficient application of force. For example, insertion of a shaft of an insertion device or medical device with too much force may cause perforation of body tissue via the shaft, while insufficient force during insertion may result in insufficient passage of the shaft through or within the body of a patient. Additionally, withdrawal of a shaft of an insertion device or medical device with too much force may cause tissue damage (e.g., via removal of a sizable kidney stone) or collapse of a body lumen, while insufficient force during withdrawal may result in insufficient retraction of the shaft from the body of a patient.

The systems, devices, and methods of the current disclosure may rectify some of the deficiencies described above or address other aspects of the prior art.

SUMMARY

Examples of the present disclosure relate to, among other things, medical devices. Each of the examples disclosed herein may include one or more of the features described in connection with any of the other disclosed examples.

In one example, a device may include a first portion coupled to a shaft of an insertable medical device. The first portion may extend along a first portion longitudinal axis between a proximal end and a distal end. The first portion may include a protrusion extending radially outwardly of the first portion longitudinal axis. At least a portion of the first portion may be received within a lumen of a second portion. The second portion may be axially moveable along the first portion longitudinal axis relative to the first portion. The second portion may include a longitudinally extending channel. A spring may be located radially between the first portion and the second portion.

Examples of the device may include one or more of the following features. The protrusion of the first portion may be received within the channel of the second portion. The protrusion may be a first protrusion, and the first portion may include a second protrusion extending radially outwardly of the first portion longitudinal axis. The second protrusion may be spaced 180° from the first protrusion, about the first portion longitudinal axis. The channel may be a first channel, and the second portion may include a second longitudinally extending channel. The second channel may be spaced 180° from the first channel, about the first portion longitudinal axis. The first portion may include a first grip portion, a base portion, and a transition portion between the first grip portion and the base portion. The base portion may have a radial dimension smaller than the first grip portion. The transition portion may include an abutment for a first end of the spring. The second portion may include a stop, wherein the stop may include an abutment for a second end of the spring. A cap may have a stem threadably received within a first side of a lumen of the first portion. A compressible grommet may be positioned axially between the stem and a second side of the lumen of the first portion. Each of the first portion and second portion may include a hexagonal or octagonal outer profile. The protrusion may be positioned on a deflectable arm of the first portion. The second portion may include a plurality of indicia, and each of the indicia may be indicative of a force exerted by the spring on the first portion and second portion. The first portion and the second portion may be located on a proximalmost third of the shaft.

In a further example, a system is described. The system may include a shaft of an insertion device or a medical device and a force indicator coupled to the shaft. The force indicator may include a first portion extending along a first portion longitudinal axis between a proximal end and a distal end and a second portion. At least a portion of the first portion may be received within a lumen of the second portion. The second portion may be axially moveable along the first portion longitudinal axis relative to the first portion and the shaft. A spring may be located radially between the first portion and the second portion.

Examples of the system may further include one or more of the following features. The first portion of the force indicator may include a protrusion extending radially outwardly of the first portion longitudinal axis and the second portion may include a longitudinally extending channel. The protrusion may be disposed within the channel and axially translatable therein. The second portion may include a plurality of indicia, each of the indicia may be indicative of a force exerted by the spring on the first portion and second portion. The first portion may include a first grip portion, a base portion, and a transition portion between the first grip portion and the base portion, where the base portion may have a radial dimension smaller than the first grip portion, and where the transition portion may include an abutment for a first end of the spring. The second portion may include a stop having an abutment for a second end of the spring. The protrusion of the first portion may be a first protrusion and the first portion may further include a second protrusion extending radially outwardly of the first portion longitudinal axis, and where the channel of the second portion may be a first channel, and the second portion may further include a second longitudinally extending channel.

In a further example, a method of measuring at least one of an insertion or a withdrawal force of a shaft is disclosed.

The method may include coupling a force indicator to the shaft. The force indicator may include a first portion which may have a protrusion extending radially outwardly of a first portion longitudinal axis and a second portion. At least a portion of the first portion may be received within a lumen of the second portion, and the second portion may include a longitudinally extending channel. The force indicator also may include a spring located radially between the first portion and the second portion. The method additionally may include moving the channel of the second portion relative to the protrusion of the first portion along the first portion longitudinal axis and determining a force exerted by the spring on the first portion and the second portion by gauging the position of the protrusion of the first portion with respect to one of a plurality of indicia on the second portion.

Examples of the method may include one or more of the following features. Coupling the force indicator to the shaft may include fixedly coupling the force indicator to the shaft via at least one of adhesives or welding. Coupling the force indicator to the shaft may include removably coupling the force indicator to the shaft via a compressible grommet.

Both the foregoing general description and the following detailed description are exemplary and explanatory only and are not restrictive of the features, as claimed. As used herein, the terms "comprises," "comprising," or other variations thereof, are intended to cover a non-exclusive inclusion such that a process, method, article, or apparatus that comprises a list of elements does not include only those elements, but may include other elements not expressly listed or inherent to such a process, method, article, or apparatus. Additionally, the term "exemplary" is used herein in the sense of "example," rather than "ideal." As used herein, the terms "about," "substantially," and "approximately," indicate a range of values within +/−5% of a stated value.

BRIEF DESCRIPTION OF THE DRAWINGS

The accompanying drawings, which are incorporated in and constitute a part of this specification, illustrate exemplary features of the present disclosure and together with the description, serve to explain the principles of the disclosure.

DETAILED DESCRIPTION

Examples of the present disclosure relate to medical systems and devices for diagnosing and/or treating internal areas of a patient's body. The medical system may include an insertion device and one or more medical devices operably coupled thereto for introduction of an end-effector or other object through the insertion device.

Reference will now be made in detail to examples of the present disclosure described above and illustrated in the accompanying drawings. Wherever possible, the same reference numbers will be used throughout the drawings to refer to the same or like parts.

The terms "proximal" and "distal" are used herein to refer to the relative positions of the components of an exemplary medical device or insertion device. When used herein, "proximal" refers to a position relatively closer to the exterior of the body or closer to a medical professional using the medical device or insertion device. In contrast, "distal" refers to a position relatively further away from the medical professional using the medical device or insertion device, or closer to the interior of the body.

Figure 1:
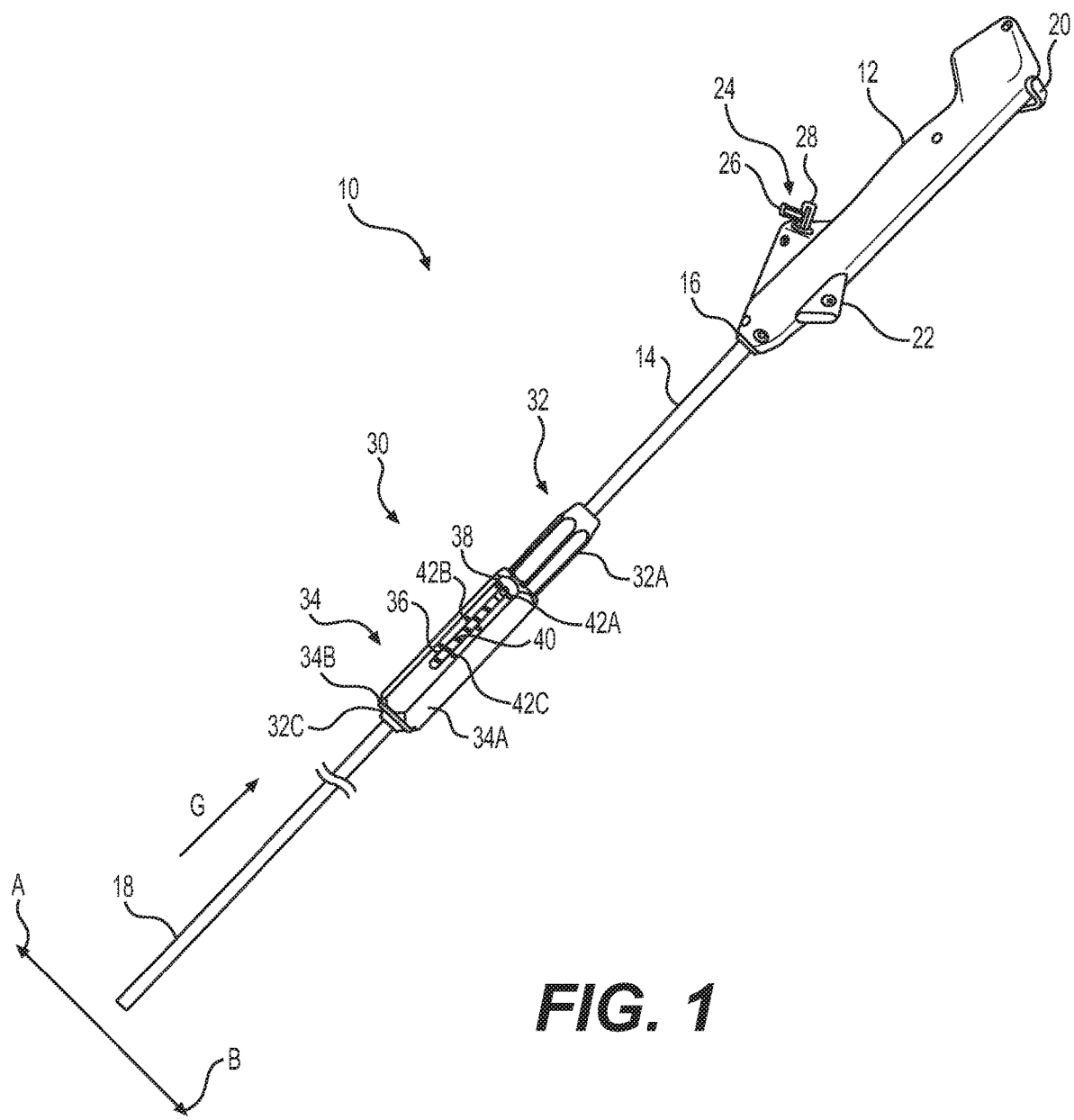
FIG. 1 illustrates an exemplary insertion device including a force indicator arranged to gauge a withdrawal force.

FIG. 1 illustrates an exemplary insertion device 10 including a handle 12 coupled to a shaft 14. Insertion device 10 includes any device configured to allow a medical professional to perform medical diagnoses and/or treatments on a patient. For example, insertion device 10 includes any device configured to allow a user to access and view internal areas of a patient's body. Additionally or alternatively, insertion device 10 may itself be a medical device and/or include any device configured to deliver one or more medical devices, such as, for example, biopsy forceps, graspers, baskets, snares, probes, scissors, retrieval devices, lasers, and/or other tools, into a patient's body. Insertion device 10 may be inserted into one of a variety of body openings, lumens, and/or cavities. For example, insertion device 10 may be inserted into any portion of a urinary tract, such as a ureter, a gastrointestinal lumen, such as an esophagus, a vascular lumen, and/or an airway.

According to aspects of the present disclosure, insertion device 10 is a ureteroscope. In some contemplated examples, insertion device 10 is a sterile, single-use, and disposable ureteroscope. Alternatively, insertion device 10 is a multiple-use, non-disposable ureteroscope. Other types of devices, however, may be substituted for the ureteroscope, including, as examples, a hysteroscope, a uteroscope, a bronchoscope, a cystoscope, and similar devices. Such devices may be single-use and disposable, or multiple-use.

Handle 12 of insertion device 10 may have any shape suitable for gripping and controlling insertion device 10. For example, handle 12 may have an ergonomic shape designed to be held comfortably in the hand, e.g., the palm of the hand of a medical professional. Shaft 14 may extend from a proximal end 16 to a distal end 18 such that proximal end 16 of shaft 14 is coupled to (e.g., detachably or permanently connected to) a distal end of handle 12. Insertion device 10 includes a steering mechanism for deflecting shaft 14 along one or more planes. For example, handle 12 includes an actuator 20 coupled to one or more portions of shaft 14 at or near distal end 18 via one or more control members, such as steering wires (e.g., Bowden cables, not shown). Any suitable steering mechanism and/or actuators may be used. Upon manipulation of actuator 20, a medical professional may selectively deflect distal end 18 of shaft 14 in a first direction A or a second direction B along a deflection plane transverse to the longitudinal axis of handle 12. As shown, actuator 20 may be located along an enlarged proximal end of handle 12. Such an enlargement may be useful to facilitate grasping of handle 12. For instance, when held upright, the enlarged proximal end of handle 12 may rest on a portion of the medical professional's hand so as to improve grasping of handle 12.

Shaft 14 includes at least one working channel (not shown) extending between proximal end 16 and distal end 18 of shaft 14. In some examples, shaft 14 may include one or more electronic components, such as a camera or other imaging device, a light source, and/or a sensor (not shown). Additionally or alternatively, shaft 14 may include a lumen for light delivery and/or steering control members (not shown) associated with actuator 20 for steering shaft 14.

Handle 12 also includes an umbilicus hub or connector 22 for facilitating electrical connections and functions, such as transferring data and/or powering a light source. In addition, handle 12 includes at least one port 24 (e.g., a T-shaped or Y-shaped luer port connection). Port 24 includes a first branch 26. First branch 26 may be fluidly coupled to one or more sources of irrigation and/or suction fluid. Accordingly, irrigation fluid (not shown) may be delivered (e.g., pumped) through the working channel via first branch 26 to provide lubrication and/or aid in visualization. Port 24 also includes a second branch 28 in communication with the working channel, e.g., to allow for the insertion of one or more medical device(s) through the working channel to distal end 18 of shaft 14. For example, second branch 28 may comprise a medical (e.g., threaded) or slip luer port through which an end-effector, control member, and/or sheath of medical device (not shown) may be delivered into second branch 28 and the working channel.

As shown in FIG. 1, a force indicator 30 is coupled to shaft 14. Force indicator 30 may be arranged and/or positioned so as to measure at least one of the removal force imparted to the body of a patient during removal or withdrawal of shaft 14 from the body, or the insertion force imparted to the body of a patient during insertion of shaft 14 into or through body. In the arrangement shown in FIG. 1, force indicator 30 is arranged so as to measure the removal force imparted to the body of the patient during removal or withdrawal of shaft 14 from the body. Force indicator 30 may be coupled to shaft 14 along any portion of shaft 14 such as, e.g., adjacent or near handle 12 and/or on or along a proximalmost third of the shaft. Further, it is understood that force indicator 30 may be positioned closer to or further distally of handle 12, but located so as to remain exterior of the body of a patient during use by a medical professional.

Figure 2:
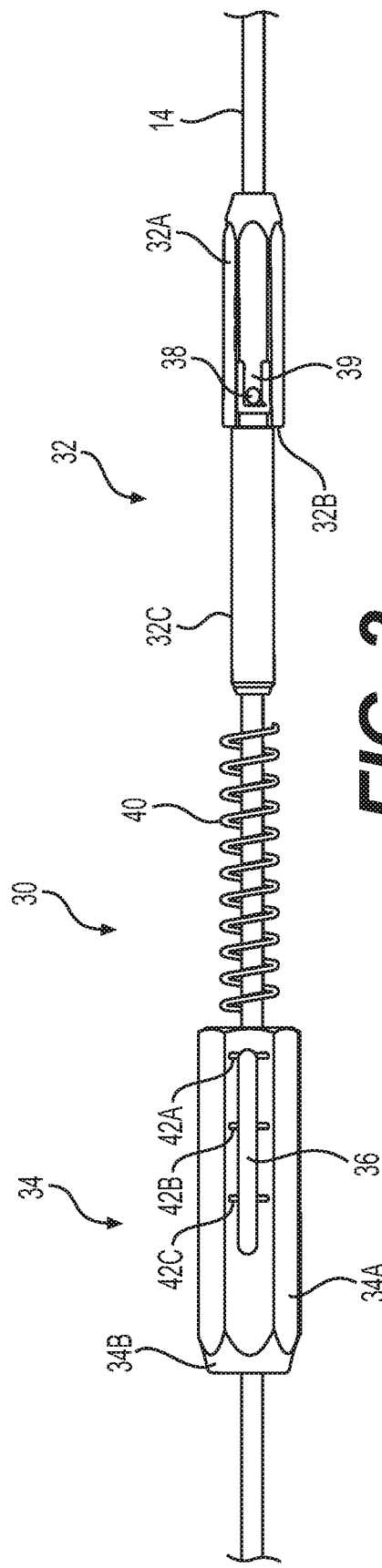
FIG. 2 illustrates a partial exploded view of the insertion device of FIG. 1.

As shown in FIGS. 1 and 2, force indicator 30 includes a first portion 32 fixed to shaft 14. For example, first portion 32 includes a lumen (not shown) extending therethrough within which shaft 14 is received and secured. That is, first portion 32 may be glued, welded, or otherwise fixedly coupled to (e.g., axially fixed and not moveable along the length of) shaft 14. Additionally, force indicator 30 includes a second portion 34 moveable with respect to shaft 14 (e.g., not fixedly coupled to shaft 14, and is axially moveable along the length of shaft 14). Second portion 34 includes at least one slot or channel 36 within which a pin, knob, and/or protrusion 38 of first portion 32 is positioned. For example, second portion 34 may include two diametrically opposed channels 36 (e.g., two channels spaced 180° apart from one another about a longitudinal axis of second portion 34). Additionally, first portion 32 may include two diametrically opposed protrusions 38 (e.g., two protrusions spaced 180° apart from one another about a longitudinal axis of first portion 32), each protrusion 38 being received within a corresponding one of the two channels 36. Each protrusion 38 may extend radially outwardly (e.g., radially away from a longitudinal axis) of first portion 32. Additionally, each protrusion 38 may be positioned on a deflectable arm 39 of first portion 32. Deflectable arms 39 extend from (e.g., is cantilevered from) first portion 32 such that they may be deflected radially inwardly (e.g., toward a longitudinal axis of first portion 32) and radially outwardly (e.g., away from a longitudinal axis of first portion 32). In order to facilitate assembly, deflectable arms 39 may deflect radially inwardly as second portion 34 is moved over first portion 32 (e.g., as first portion 32 is received within the lumen of second portion 34). Once channels 36 align with protrusions 38, deflectable arms 39 may deflect radially outwardly to secure first portion 32 and second portion 34 together via interaction between protrusions 38 and channels 36. That is, once assembled, protrusions 38 are retained within channels 36, thereby coupling first portion 32 and second portion 34 of force indicator 30 together.

Further, second portion 34 includes a plurality of force indication markings or indicia 42A-42C. In use, second portion 34 may be moved relative to first portion 32 such that channel 36 may move relative to protrusion 38. In such a manner, protrusion 38 may translate along channel 36 and align with one of indicia 42A-42C to indicate a degree or amount of force being applied to the body of the patient, as will be described in further detail below.

Each of first portion 32 and second portion 34 may have a grip surface on a radially external surface thereof to facilitate accurate and secure placement of a medical professional's hand along force indicator 30. For example, as shown in FIGS. 1 and 2, first portion 32 includes a first grip portion 32A and second portion 34 includes a second grip portion 34A which is shaped or otherwise configured to facilitate secure and accurate grasping by the medical professional. That is, each of first grip portion 32A and second grip portion 34A may have a ribbed, hexagonal, octagonal or any other such shape. In other words, each of first grip portion 32A and second grip portion 34A may be shaped in a manner similar to that of a shaft of a pencil. In use, torque may be transferred from the hand of a medical professional to second portion 34, then to first portion 32, and then to shaft 14. Alternatively, torque may be transferred from the hand of the medical professional to an inner surface of a lumen (not shown) of the second portion 34, to first portion 32, and then to shaft 14.

While each of first portion 32 and second portion 34 are illustrated to include a grip portion, e.g., first grip portion 32A and second grip portion 34A, respectively, in some arrangements, only one or neither of first portion 32 and second portion 34 may include such a grip portion. Additionally, while substantially the entire length of the radially exterior surface of second portion 34 is shown to include second grip portion 34A, in other arrangements, less than substantially the entire length of the radially exterior surface of second portion 34 may include second grip portion 34A. For example, in some arrangements, second grip portion 34A may extend along about three fourths, about half, or about a quarter of the entire length of the radially external surface of second portion 34.

Further, as shown in FIG. 2, first portion 32 includes a flange, surface, or transition portion 32B and a base portion 32C. Base portion 32C includes a radial dimension (e.g., diameter) smaller than that of first grip portion 32A while transition portion 32B is arranged axially between first grip portion 32A and base portion 32C. In addition, second portion 34 includes an abutment or stop 34B. Stop 34B may include a radially narrowed or tapered flange forming an abutment for an elastic member or spring 40 (e.g., a helical compression spring). Spring 40 is positioned radially between first portion 32 and second portion 34. That is, spring 40 may be positioned about (e.g., radially outwardly of a longitudinal axis of first portion 32) base portion 32C of first portion 32, and radially inwardly of and/or within the lumen of second portion 34. A proximal end of spring 40 abuts transition portion 32B of first portion 32 while a distal end of spring 40 abuts stop 34B of second portion 34. In such a manner, movement of second portion 32 relative to first portion 32 compresses or stresses spring 40.

Spring 40 includes a known spring constant k. For example, spring 40 may have a spring constant k selected to achieve a desired range of restoring force F, e.g., between about 0 lbF and about 10 lbF, or between about 0 lbF and about 5 lbF, or between about 0 lbF and about 3 lbF. That is, spring 40 may be designed to have a selected or desired range of restoring force F and a particular spring constant k may be selected to achieve such a desired range of restoring force F. In one example, spring constant k may be between about 3 and about 15, or between about 5 and about 10, or about 5, or about 10. Further, spring 40 may have a known free length (e.g., a total or entire length between the proximal-most end and distal-most end of spring 40 when spring 40 is in a natural, unbiased, unstressed and/or neutral state). For example, spring 40 may have a free length selected to achieve a desired range of restoring force F. That is, as noted above, spring 40 may be designed to have a selected or desired range of restoring force F and a particular free length may be selected to achieve such a desired range of restoring force F. In one example, the free length may be between about 0.5 inches (1.27 cm) and about 3 inches (7.62 cm), between about 1 inch (2.54 cm) and about 2 inches (5.08 cm), about 1 inch (2.54 cm), or about 1.3 inches (3.302 cm). Additional variables may also be selected so as to achieve a desired range of restring force F. Such variables may include spring wire diameter, spring outside diameter, number of active coils, total number of coils, spring material, etc.

Accordingly, a restoring force F of spring 40 may be calculated using Hooke's Law in which the restoring (e.g., reaction) force F exerted by spring 40 on an object that is tensioning or compressing spring 40 (e.g., the medical professional and/or first portion 32 and second portion 34) by some distance X is proportional to that distance.

That is:

$$F=-kX$$

where k is the spring constant, e.g., the stiffness of spring 40, and X is the length of deformation of spring 40.

During withdrawal of shaft 14 from the body of a patient, the medical professional may grasp second grip portion 34A and pull second grip portion 34A in the direction G, as shown in FIG. 1. Upon overcoming an initial load of spring 40 (e.g., the load experienced by spring 40 when protrusion 38 is aligned with first indicia 42A, or a load on spring 40 due to being positioned between first portion 32 and second portion 34 of force indicator 30), second portion 34 will move in the direction G such that first indicia 42A is moved proximally of protrusion 38 while second indicia 42B is move into alignment with or closer to protrusion 38. That is, as a medical professional retracts second portion 34 proximally in the direction G, he or she will overcome the initial spring bad of spring 40 until second indicia 42B is aligned with protrusion 38 thereby indicating an increase in withdrawal force is being exerted to the body of the patient. Upon application of larger (e.g., greater magnitude) force in the direction G, second portion 34 will move in the direction G such that second indicia 42B is moved proximally of protrusion 38 while third indicia 42C is moved into alignment with or closer to protrusion 38. That is, as a medical professional further retracts second portion 34 proximally in the direction G, he or she will overcome the spring load of spring 40 when protrusion 38 is aligned with second indicia 42B until third indicia 42C is aligned with one protrusion 38 thereby indicating an additional increase in withdrawal force is being exerted to the body of the patient.

In other words, when protrusion 38 is aligned with first indicia 42A, spring 40 is subject to an initial load. When protrusion 38 is aligned with second indicia 42B, the medical professional is applying a force to the body of the patient via shaft 14 and spring 40 equal to the compression force of spring 40 when compressed by a length difference between first indicia 42A and second indicia 42B. When protrusion 38 is aligned with third indicia 42C, the medical professional is applying a force to the body of the patient via shaft 14 and spring 40 equal to the compression force of spring 40 when compressed by a length difference between first indicia 42A and third indicia 42C. The spacing between first indicia 42A, second indicia 42B, and third indicia 42C may be selected to correspond with a desired level of force being applied to the body of the patient during withdrawal. Additionally, while spacing between indicia 42A-42C is illustrated as equal, the disclosure is not so limited. In some arrangements, an axial length along second portion 34 between first indicia 42A and second indicia 42B may be longer than an axial length along second portion 34 between second indicia 42B and third indicia 42C, or vice versa. Additionally, while only three indicia 42A-42C are illustrated, the disclosure is not so limited. For example, second portion 34 may include greater or fewer indicia markings such as, e.g., between about 2 and about 10 indicia markings.

Figure 3:
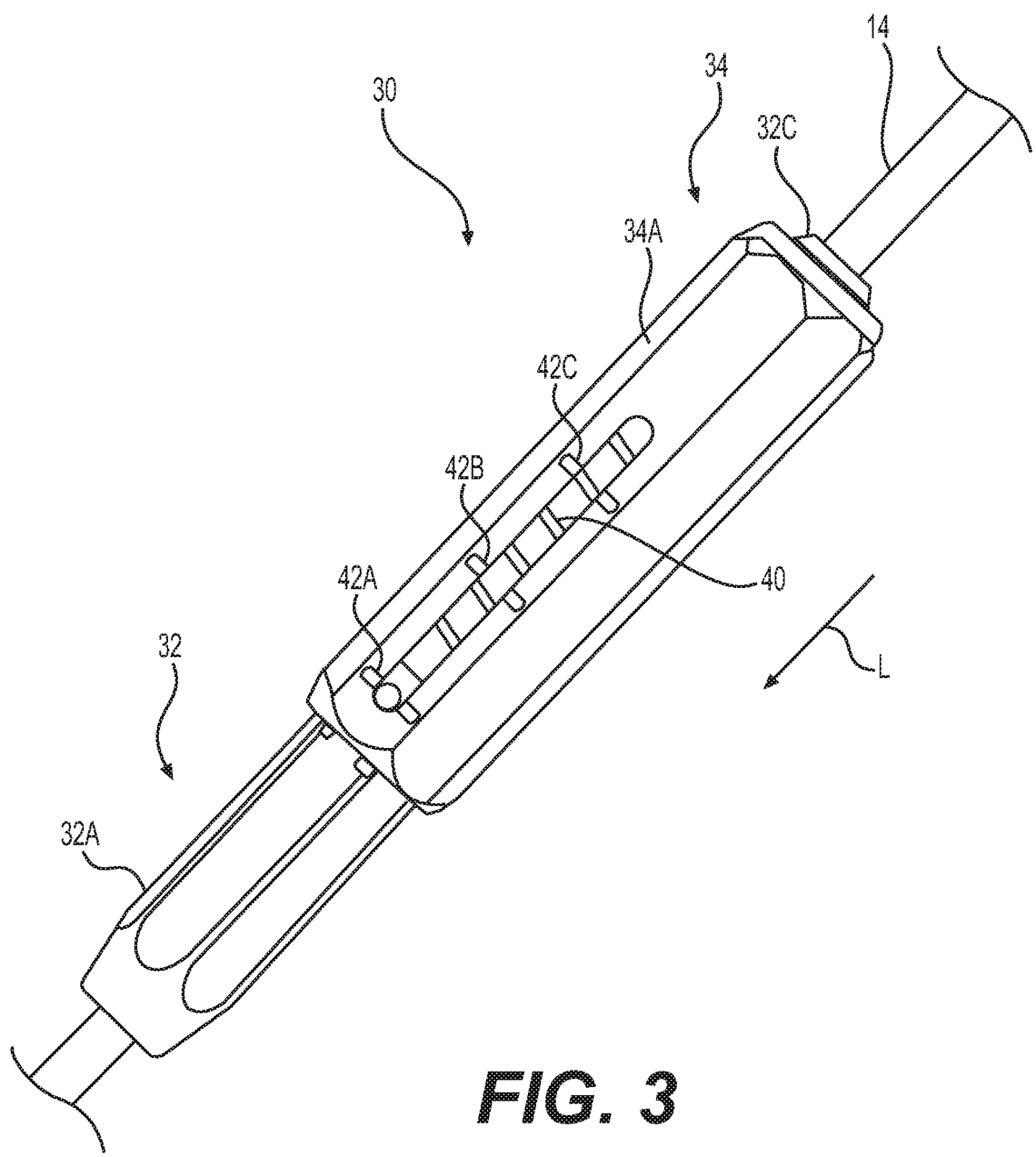
FIG. 3 illustrates a partial view of an insertion device including a force indicator arranged to gauge an insertion force, according to further aspects of the disclosure.

As noted above, force indicator 30 may be arranged and/or positioned so as to measure at least one of the removal force imparted to the body of a patient during removal or withdrawal of shaft 14 from the body of the patient, or the insertion force imparted to the body of a patient during insertion of shaft 14 into or through the body. While force indicator 30 of FIGS. 1 and 2 is illustrated to measure the withdrawal force, in a further arrangement, as shown in FIG. 3, force indicator 30 may be arranged to measure insertion force imparted to the body of a patient during insertion of shaft 14 into or through body. In so doing, the direction of force indicator 30 may be reversed. In other words, rather than first grip portion 32A of first portion 32 being arranged proximally of base portion 32C of first portion 32, in the arrangement shown in FIG. 3, first grip portion 32A of first portion 32 is arranged distally of base portion 32C of first portion 32. In such a manner, during insertion of shaft 14 into the body of a patient, the medical professional may grasp second grip portion 34A and push second grip portion 34A in the direction L, as shown in FIG. 3. It is understood that direction L is opposite of direction G shown in FIG. 1. Upon overcoming an initial load of spring 40 (e.g., the load experienced by spring 40 when protrusion 38 is aligned with first indicia 42A, or a load on spring 40 due to being positioned between first portion 32 and second portion 34 of force indicator 30), second portion 34 will move in the direction L such that first indicia 42A is moved distally of protrusion 38 while second indicia 42B is move into alignment with or closer to protrusion 38. That is, as a medical professional advances second portion 34 distally in the direction L, he or she will overcome the initial spring load of spring 40 until second indicia 42B is aligned with protrusion 38 thereby indicating an increase in insertion force is being exerted to the body of the patient. Upon application of larger (e.g., greater magnitude) force in the direction L, second portion 34 will move in the direction L such that second indicia 42B is moved distally of protrusion 38 while third indicia 42C is moved into alignment with or closer to protrusion 38. That is, as a medical professional further advances second portion 34 distally in the direction G, he or she will overcome the spring load of spring 40 when protrusion 38 is aligned with second indicia 42B until third indicia 42C is aligned with one protrusion 38 thereby indicating an additional increase in insertion force is being exerted to the body of the patient. In other words, when protrusion 38 is aligned with first indicia 42A, spring 40 is subject to an initial load. When protrusion 38 is aligned with second indicia 423, the medical professional is applying a force to the body of the patient via shaft 14 and spring 40 equal to the compression force of spring 40 when compressed by a length difference between first indicia 42A and second indicia 42B. When protrusion 38 is aligned with third indicia 42C, the medical professional is applying a force to the body of the patient via shaft 14 and spring 40 equal to the compression force of spring 40 when compressed by a length difference between first indicia 42A and third indicia 42C.

Figure 4:
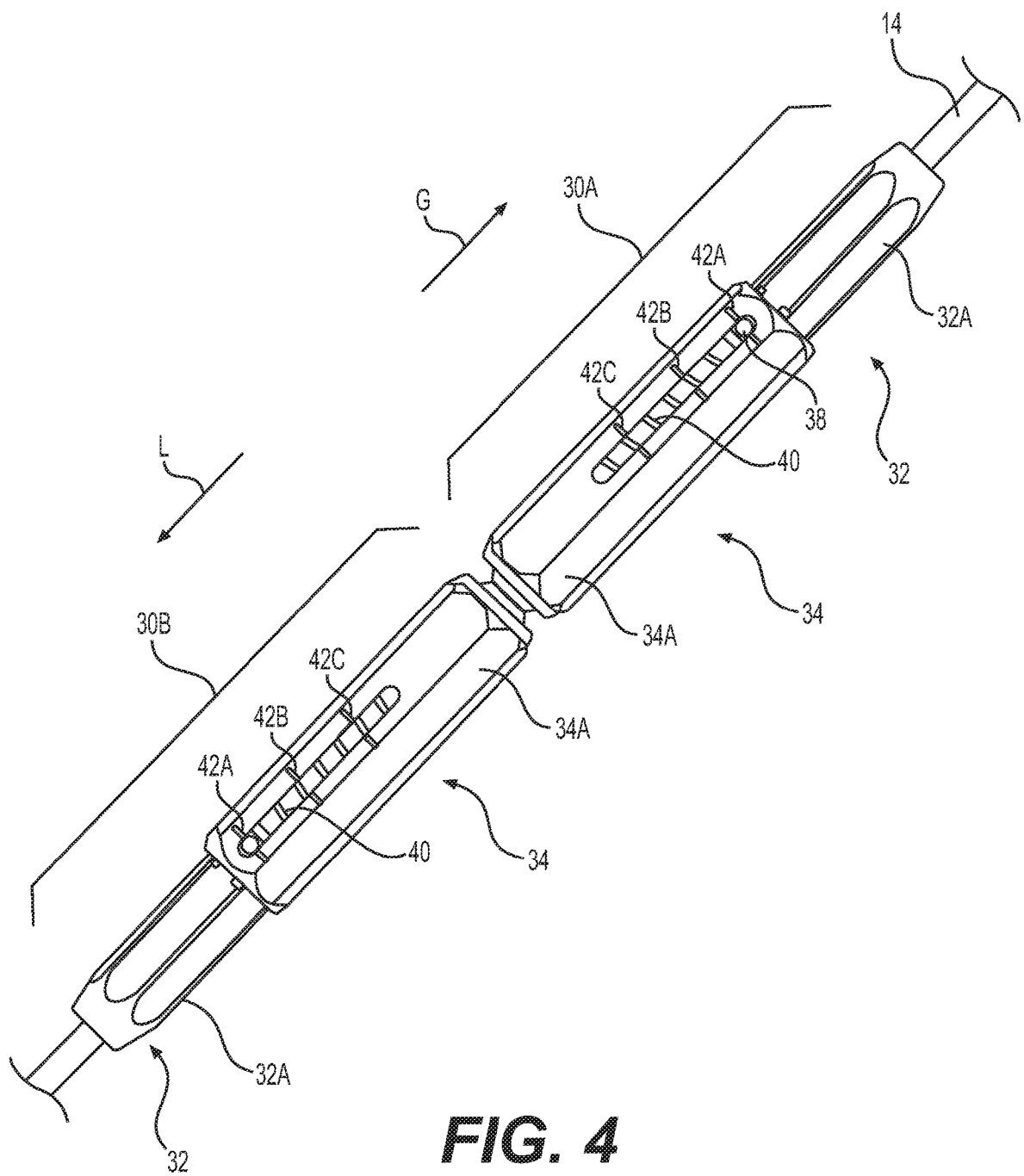
FIG. 4 illustrates an additional exemplary partial view of an insertion device including a plurality of force indicators, according to further aspects of the disclosure.

FIG. 4 illustrates an additional arrangement in which a plurality of force indicators are arranged along shaft 14. Indeed, as shown, a first force indicator 30A may be arranged so as to measure the removal force imparted to the body of the patient during removal or withdrawal of shaft 14 from the body. Additionally, a second force indicator 30B may be arranged to measure insertion force imparted to the body of a patient during insertion of shaft 14 into or through body. That is, in the arrangement shown in FIG. 4, during insertion of shaft 14 into the body of a patient, a medical professional may grasp second grip portion 34A of second force indicator 30B, and advance second portion 34 in the direction L, in a manner similar to that as described in connection with FIG. 3. During withdrawal of shaft 14 from the body of a patient, a medical professional may grasp second grip portion 34A of first force indicator 30A, and retract second portion 34 in the direction G, in a manner similar to that as described in connection with FIGS. 1 and 2.

Figure 5:
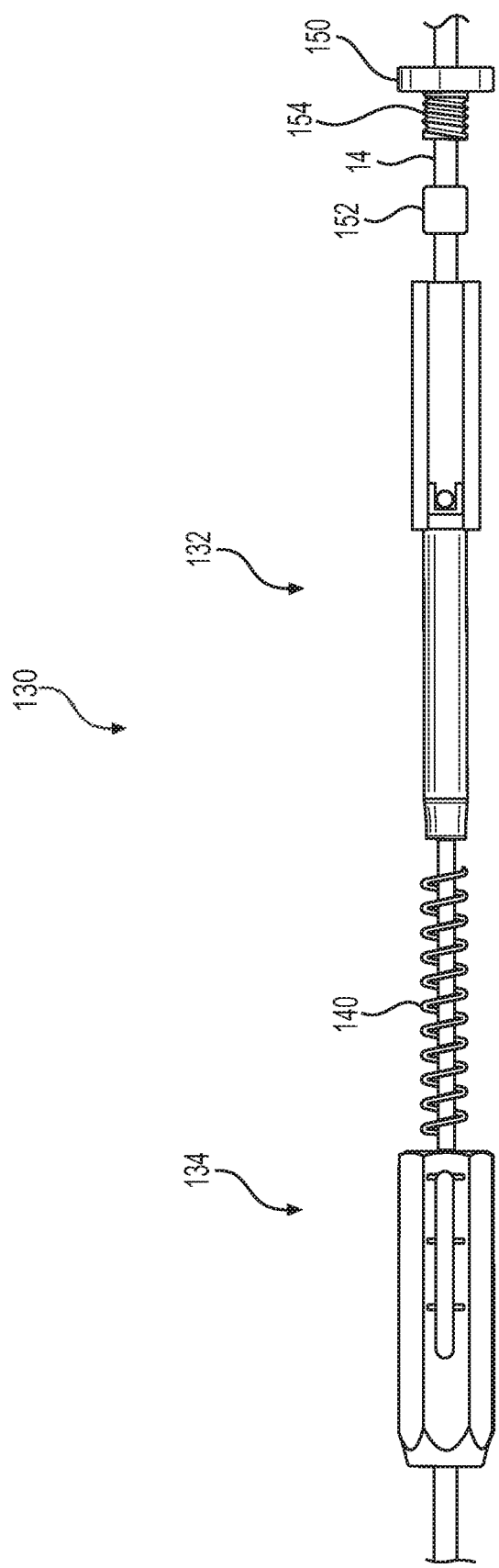
FIG. 5 illustrates a partial exploded view of an insertion device including an adjustable force indicator, according to further aspects of the disclosure.

As noted in each of the arrangements of FIGS. 1-4, first portion 32 is fixedly coupled to shaft 14. That is, first portion 32 may be glued, welded, or otherwise fixedly coupled to (e.g., axially fixed and not moveable along the length of) shaft 14. In an alternative arrangement, as shown in FIG. 5, a first portion 132 of a force indicator 130 may be selectively coupleable and uncoupleable from shaft 14. The force indicator 130 of FIG. 5 includes similar features to that of FIG. 1 and accordingly, like parts will be numbered with the same reference number plus 100. That is, force indicator 130 includes a first portion 132, a second portion 134, and a spring 140 therebetween. Rather than being fixedly coupled to shaft 14 in a manner similar to first portion 32, first portion 132 includes a cap 150 and compressible grommet 152 for selectively coupling and uncoupling first portion 132 to or from shaft 14. Cap 150 defines a lumen (not shown) extending therethrough and within which shaft 14 may be received. Additionally, cap 150 includes a threaded stem 154 which may be received within a lumen (not shown) of first portion 132. At least a portion of the lumen of first portion 132 may be similarly threaded for engagement with stem 154 of cap 150. Additionally, grommet 152 may be comprised of a compressible material such as, e.g., rubber. Upon threading or otherwise coupling stem 154 of cap 150 in the lumen (not shown) of first portion 132, grommet 152 may compress, pinch, or otherwise grip shaft 14. In such a manner, shaft 14 may be fixedly coupled to force indicator 130. Additionally, unscrewing or otherwise uncoupling cap 150 from first portion 132 may enable grommet 152 to release shaft 14. As such, a position of shaft 14 relative to force indicator 130 may be adjusted, as needed. Additionally, while force indicator 130 is arranged for measuring withdrawal force, e.g., in a similar direction as that of force indicator 30 of FIGS. 1 and 2, the disclosure is not so limited. Rather, any of the arrangements of FIGS. 1-4 may be arranged to include a releasable cap 150 and grommet 152 of FIG. 5.

In use, a medical professional may grasp one force indicator 30, 130 so as to gauge an insertion or withdrawal force of shaft 14. In such a manner, the medical professional will be readily provided with a visual aid depicting the degree of force imparted to the body of a patient. As the force indicator provides real-time information to the medical professional during use, he or she may readily adjust an insertion or withdrawal force, as appropriate to avoid unnecessary trauma to a patient.

While principles of the present disclosure are described herein with reference to illustrative examples for particular applications, it should be understood that the disclosure is not limited thereto. Those having ordinary skill in the art and access to the teachings provided herein will recognize additional modifications, applications, embodiments, and substitution of equivalents all fall within the scope of the features described herein. Accordingly, the claimed features are not to be considered as limited by the foregoing description.

I claim:

1. A method of measuring an insertion force and a withdrawal force of a shaft of a device, the method comprising:
coupling a force indicator to the shaft, the force indicator including:
a first portion having a protrusion extending radially outwardly of a first portion longitudinal axis;
a second portion distal to the first portion, at least a portion of the first portion being received within a lumen of the second portion, wherein the second portion includes a longitudinally extending channel; and
a spring located between the first portion and the second portion;
inserting the shaft into a body;
withdrawing the shaft from the body;
moving the channel of the second portion relative to the protrusion of the first portion along the first portion longitudinal axis during the insertion and withdrawal of the shaft from the body, thereby compressing the spring;
determining a first force exerted by the spring on the first portion and the second portion by gauging the position of the protrusion of the first portion with respect to one of a plurality of indicia on the second portion, wherein the first force exerted by the spring is indicative of the insertion force of the shaft; and
determining a second force exerted by the spring on the first portion and the second portion by gauging the position of the protrusion of the first portion with respect to one of a plurality of indicia on the second portion, wherein the second force exerted by the spring is indicative of the withdrawal force of the shaft.

2. The method of claim 1, wherein coupling the force indicator to the shaft includes fixedly coupling the force indicator to a proximal-most third of the shaft via at least one of adhesives or welding.

3. The method of claim 1, wherein coupling the force indicator to the shaft includes removably coupling the force indicator to the shaft via a compressible grommet.

4. The method of claim 1, wherein withdrawing the shaft from the body includes grasping the second portion and translating the second portion in a direction relative to the first portion, thereby compressing the spring and moving the channel of the second portion relative to the protrusion of the first portion.

5. The method of claim 4, wherein the position of the protrusion of the first portion with respect to one of the plurality of indicia on the second portion indicates a distance by which the spring compresses.

\* \* \* \* \*